(12) United States Patent
Muse

(10) Patent No.: US 9,592,374 B2
(45) Date of Patent: Mar. 14, 2017

(54) CATHETER ADAPTER HAVING UV-C ANTIMICROBIAL RADIATION SOURCE AND ACCESS WINDOW WITHIN CATHETER LUMEN FOR INTRAVENOUS THERAPY

(75) Inventor: Jay Muse, Centerville, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 327 days.

(21) Appl. No.: 13/223,174

(22) Filed: Aug. 31, 2011

(65) Prior Publication Data
US 2012/0053512 A1    Mar. 1, 2012

Related U.S. Application Data

(60) Provisional application No. 61/378,976, filed on Sep. 1, 2010.

(51) Int. Cl.
*A61M 39/16* (2006.01)
*A61M 39/10* (2006.01)

(52) U.S. Cl.
CPC ..... *A61M 39/16* (2013.01); *A61M 2039/1077* (2013.01); *A61M 2039/167* (2013.01); *Y10T 29/49826* (2015.01)

(58) Field of Classification Search
CPC ............... A61B 18/18; A61M 1/1674; A61M 2039/0285; A61M 39/16
USPC ........ 604/103, 256, 265, 21, 20; 607/88–89; 128/207.14; 422/24
See application file for complete search history.

(56) References Cited

U.S. PATENT DOCUMENTS

| | | | |
|---|---|---|---|
| 3,792,703 A * | 2/1974 | Moorehead | 604/158 |
| 4,311,138 A * | 1/1982 | Sugarman | 604/165.02 |
| 4,411,648 A | 10/1983 | Davis et al. | |
| 4,765,588 A | 8/1988 | Atkinson | |
| 4,886,593 A | 12/1989 | Gibbs | |
| 5,251,873 A | 10/1993 | Atkinson et al. | |
| 5,260,020 A | 11/1993 | Wilk et al. | |
| 5,295,657 A | 3/1994 | Atkinson | |
| 5,295,658 A | 3/1994 | Atkinson et al. | |
| 5,312,813 A | 5/1994 | Costerton et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,855,203 A * | 1/1999 | Matter | 128/207.14 |
| 5,957,898 A | 9/1999 | Jepson et al. | |
| 6,171,287 B1 | 1/2001 | Lynn et al. | |
| 6,261,282 B1 | 7/2001 | Jepson et al. | |
| 6,282,444 B1 | 8/2001 | Kroll et al. | |
| 6,344,033 B1 | 2/2002 | Jepson et al. | |
| 6,416,492 B1 * | 7/2002 | Nielson | 604/22 |

(Continued)

FOREIGN PATENT DOCUMENTS

WO    WO 02/102421 A1    12/2002
WO    WO 2008/024478 A2    2/2008

*Primary Examiner* — Bhisma Mehta
*Assistant Examiner* — Matthew A Engel
(74) *Attorney, Agent, or Firm* — Jeanne Lukasavade; Craig Metcalf; Kirton McConkie

(57) ABSTRACT

A vascular access device having a fluid chamber in which UV-C radiation is emitted to irradiate pathogens contained in an infusate flowing though the fluid chamber.

15 Claims, 8 Drawing Sheets

(56) References Cited

U.S. PATENT DOCUMENTS

| | | |
|---|---|---|
| 6,428,491 B1 | 8/2002 | Weiss |
| 6,562,295 B1 | 5/2003 | Neuberger |
| 6,595,964 B2 | 7/2003 | Finley et al. |
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 6,908,460 B2 * | 6/2005 | DiStefano ............... 606/7 |
| 8,109,981 B2 * | 2/2012 | Gertner et al. ............ 607/88 |
| 8,142,713 B2 * | 3/2012 | Gordon ................... 422/22 |
| 8,496,610 B2 * | 7/2013 | Levenson et al. ......... 604/29 |
| 8,556,950 B2 * | 10/2013 | Rioux et al. ............. 607/88 |
| 2002/0056634 A1 | 5/2002 | Pitts, Jr. et al. |
| 2002/0066702 A1 | 6/2002 | Liu |
| 2002/0091424 A1 | 7/2002 | Biel |
| 2002/0123787 A1 | 9/2002 | Weiss |
| 2002/0193752 A1 | 12/2002 | Lynn |
| 2004/0116845 A1 | 6/2004 | Darouiche et al. |
| 2005/0038376 A1 | 2/2005 | Zumeris et al. |
| 2005/0095351 A1 | 5/2005 | Zumeris et al. |
| 2005/0147525 A1 | 7/2005 | Bousquet |
| 2005/0256500 A1 | 11/2005 | Fujii |
| 2006/0004317 A1 * | 1/2006 | Mauge ............ A61M 27/006 604/8 |
| 2007/0049998 A1 | 3/2007 | Conrad et al. |
| 2007/0176117 A1 * | 8/2007 | Redmond et al. ....... 250/455.11 |
| 2008/0027399 A1 | 1/2008 | Harding et al. |
| 2008/0051736 A1 * | 2/2008 | Rioux et al. .............. 604/265 |
| 2008/0306454 A1 * | 12/2008 | Sikora .............. A61L 2/10 604/265 |
| 2010/0233021 A1 * | 9/2010 | Sliwa ........... A61M 25/0017 422/20 |
| 2010/0264329 A1 * | 10/2010 | Vardiel et al. ............. 250/436 |
| 2011/0144566 A1 | 6/2011 | Dacey et al. ............... 604/21 |
| 2012/0116294 A1 * | 5/2012 | Boenig ............ A61M 1/285 604/29 |
| 2013/0303996 A1 * | 11/2013 | Rasooly ............. A61L 2/10 604/264 |
| 2015/0126976 A1 * | 5/2015 | Tang ............ A61M 25/0012 604/544 |

\* cited by examiner

CATHETER ADAPTER HAVING UV-C ANTIMICROBIAL RADIATION SOURCE AND ACCESS WINDOW WITHIN CATHETER LUMEN FOR INTRAVENOUS THERAPY

RELATED APPLICATIONS

This application claims the benefit of U.S. Provisional Application No. 61/378,976, filed Sep. 1, 2010, entitled UV-C ANTIMICROBIAL DEVICE FOR INTRAVENOUS THERAPY, which is incorporated herein by reference.

BACKGROUND OF THE INVENTION

The present disclosure relates to infusion therapy with antimicrobial vascular access devices. Infusion therapy is one of the most common health care procedures. Hospitalized, home care, and other patients receive fluids, pharmaceuticals and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The proximal end of the vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes or seals the vascular access device, and allows for intermittent infusion or injection of fluids and pharmaceuticals. An IV access device may include a housing and a septum for closing the system. The septum may be opened with a blunt cannula or a male Luer of a medical device.

Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Vascular access device infection resulting in CRBSIs may be caused by failure to regularly clean the device, a non-sterile insertion technique, or by pathogens entering the fluid flow path through either end of the path subsequent to catheter insertion. Studies have shown the risk of CRBSI increases with catheter indwelling periods. Thus, when a contaminated vascular access device or infusate is used in an infusion procedure, pathogens are allowed to enter the patient's bloodstream and cause a BSI.

The germicidal or biocidal effects of ultra violet (UV) radiation have been known since the late $19^{th}$ century and in recent years the use of UV radiation has gained broad acceptance in the fields of water and air purification and has found some limited use in food processing and medical device sterilization.

UV light consists of high energy photons which occupy the 200 to 400 nanometer wavelengths of the electromagnetic spectrum. This means that UV light emits slightly less energy than soft X-ray radiation, but significantly more than visible light. UV energy does not directly kill pathogens, but rather causes a photochemical reaction with the genetic structure which inhibits the ability of the pathogens to reproduce, therefore, in effect, killing the pathogen.

The amount of energy delivered by UV light is inversely proportional to its wavelength, therefore, the shorter the wavelength, the greater the energy produced. In general, the UV light portion of the spectrum is made up of three segments: UV-A (315-400 nm), used for sun-tanning lamps; UV-B (280-315 nm); and UV-C (200-280 nm). The UV-B and UV-C regions contain wavelengths with the best biocidal action. Studies have shown that the wavelengths most effective in killing microbes are between 250-265 nm.

When using UV-C radiation to sterilize medical devices, precautions must be taken to prevent the patient and/or physician from being exposed to the harmful UV-C radiation. Some biocidal systems and methods require the use of external covering or shields to provide adequate protection. Other systems use lower intensity biocidal lamps. However, these systems fail to provide convenient and efficient sterilization, thereby requiring that additional steps be taken to ensure complete and safe antiseptic conditions.

Thus, what are needed are systems, devices, and methods to prohibit, limit, or otherwise eliminate vascular access device and infusate contamination to reduce the risk and occurrence of CRBSIs in a safe and efficient manner. The various embodiments of the present invention meet this need.

BRIEF SUMMARY OF THE INVENTION

The present invention has been developed in response to problems and needs in the art that have not yet been fully resolved by currently available vascular access systems, devices, and methods. Thus, these developed systems, devices, and methods prohibit, limit, or otherwise eliminate vascular access device contamination to reduce the risk and occurrence of CRBSIs.

A medical device may be a vascular access device that includes a fluid chamber having an interior lumen in direct communication with an infusate flowing through the vascular access device. The fluid chamber includes an access window through which a UV-C radiation source emits UV-C radiation. The UV-C radiation passes through the access window into the interior lumen of the fluid chamber. An infusate present within the fluid chamber is thus exposed to the UV-C radiation thereby irradiating any pathogens present within the infusate.

In some implementations of the present invention, an interior surface of the fluid chamber is further modified to include a UV-C reflective coating or material whereby the UV-C radiation emitted into the interior lumen is retained and reflected within the interior lumen. This feature increases the exposure time of the infusate to the UV-C radiation thereby enabling the use of a lower powered biocidal lamp. Some implementations further include a fluid chamber comprised of a UV-C opaque material. This feature prevents leakage of UV-C radiation from the fluid chamber, thereby preventing undesirable exposure of the patient and physician to UV-C radiation.

Some implementations further comprise a reusable UV-C radiation source, wherein the UV-C radiation source is removable from the access window and compatibly inserted into an access window of a second infusion device. Implementations of the present invention further include a catheter adapter which includes an access window for receiving a UV-C radiation source.

Some implementations of the present invention further include a method for manufacturing a vascular access device, the method including steps for 1) providing a fluid chamber having an interior lumen, and interior surface and an exterior surface, 2) providing an access window through a sidewall of the fluid chamber, and 3) providing a source of UV-C radiation capable of couple to the fluid chamber such that UV-C radiation is emitted though into the interior of the fluid chamber via the access window. Some implementations further include a step for applying a UV-C reflective material to at least one of the interior surface and the exterior surface of the fluid chamber. Further, some implementations include a step for attaching the UV-C source in a housing that is configured to selectively couple to the exterior surface of the fluid chamber.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Definitions

As used herein the following terms gave the following meanings:

"Fluid Chamber" means any device having an interior volume or lumen through which an infusate passes during an infusion procedure, wherein the infusate is exposed to UV-C radiation while within the fluid chamber.

"UV-C" means ultraviolet light having a wavelength between about 200 nm and 280 nm.

"Biocidal Lamp" means a commercially available UV generating lamp that produces energy output in the range of about 200 nm to about 280 nm, with a preferred wavelength being about 255 nm.

"Vascular Access Device" means any device or combination of devices used to infuse an infusate into a patient.

"UV-C Transparent Material" means any material through which UV-C radiation or energy is permitted to pass.

"UV-C Opaque Material" means any material which blocks or otherwise prevents passage of UV-C radiation or energy.

"UV-C Reflective Material" means any material which reflects UV-C radiation or energy.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
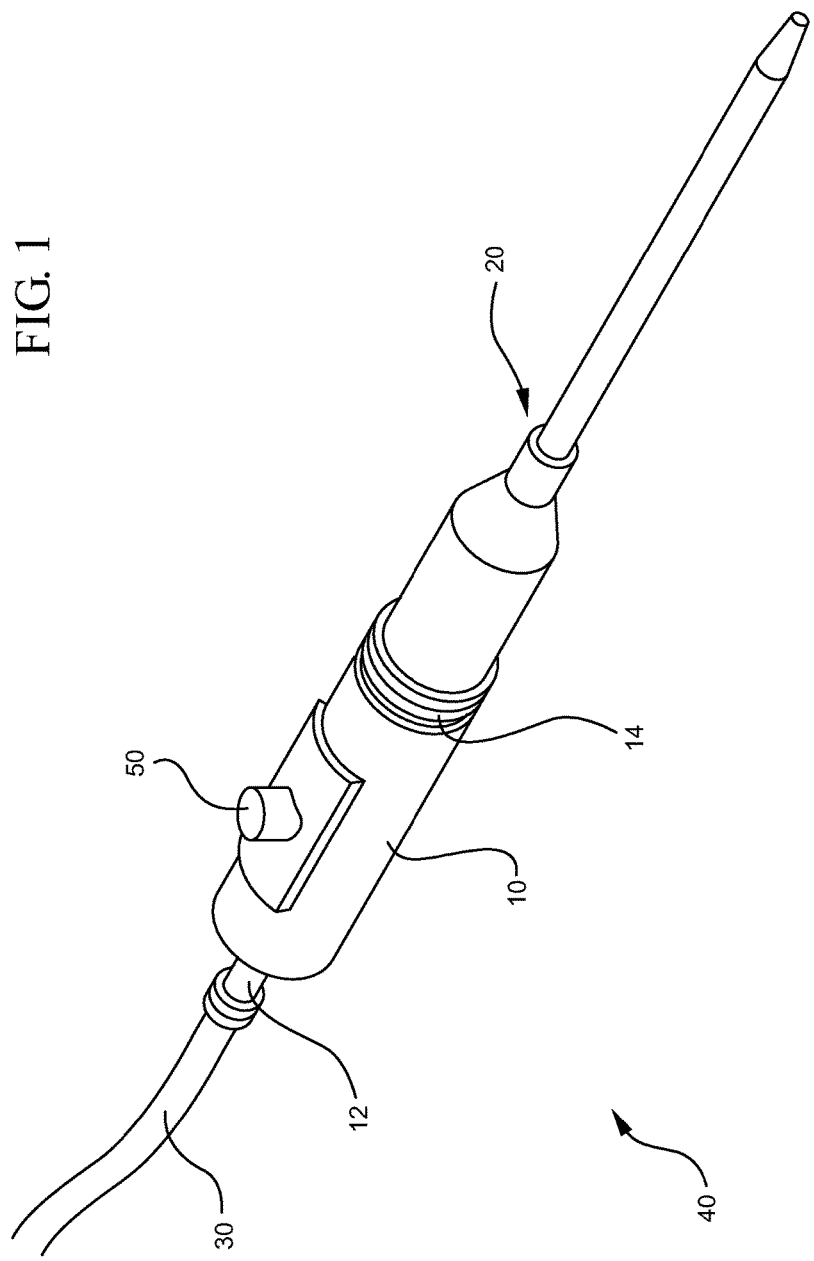
FIG. 1 is a perspective view of a fluid chamber coupled to an intravenous catheter in accordance with a representative embodiment of the present invention.

Referring now to FIG. 1, a fluid chamber 10 is shown coupled to an intravenous catheter 20 and a section of intravenous tubing 30. In general, fluid chamber 10 comprises a housing having a proximal end 12 and a distal end 14 for being placed in the fluid path of an infusion system 40. In some embodiments, proximal end 12 is coupled to intravenous tubing 30, and distal end 14 is coupled to intravenous catheter 20, such that an infusate from an intravenous bag, or other infusate source (not shown) is passed through fluid chamber 10 prior to being delivered to the patient via intravenous catheter 20. In some embodiments, proximal and distal ends 12 and 14 comprise Luer connectors whereby to form a fluid-tight connection between the adjacent components 20 and 30 of the system 40.

In general, fluid chamber 10 comprises a housing having an annular flow volume which defines an interior lumen. Fluid chamber 10 further comprises an access window (not shown) through which a UV-C source 50 emits UV-C radiation into the interior lumen of the fluid chamber. Thus, an infusate present within the interior lumen is irradiated by the UV-C radiation thereby repressing pathogenic activity and preventing or minimizing CRBSIs in the patient.

Figure 2:
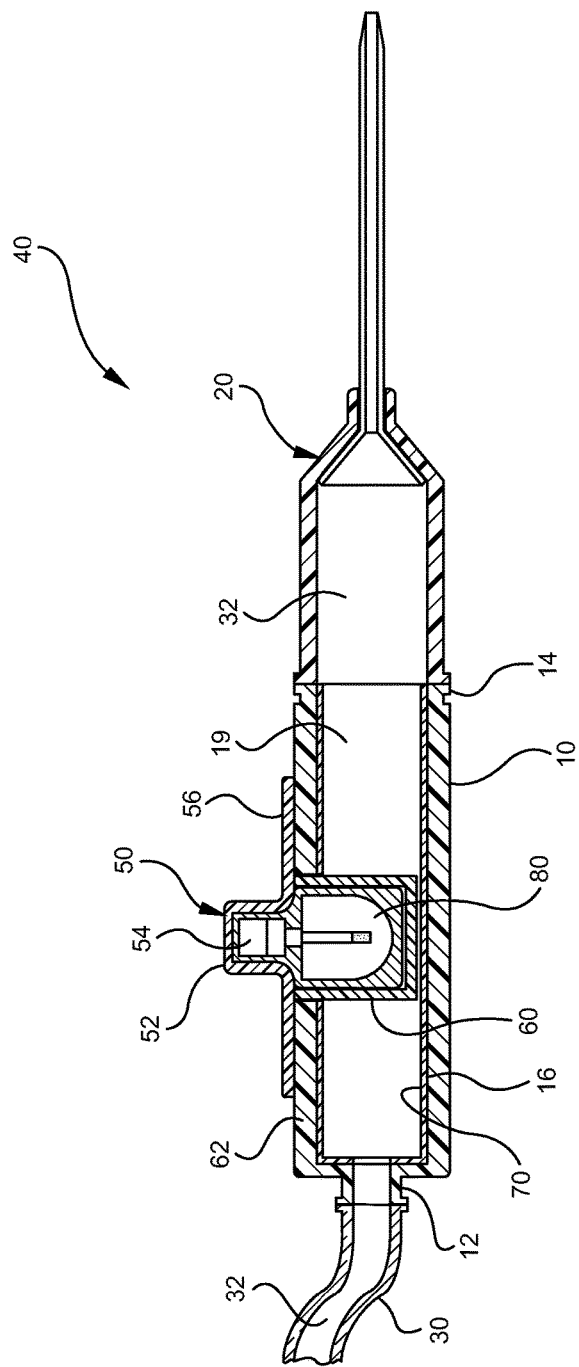
FIG. 2 is a cross section side view of a fluid chamber coupled to an intravenous catheter in accordance with a representative embodiment of the present invention.

Referring now to FIG. 2, a cross section side view of infusion system 40 is shown. In some embodiments, fluid chamber 10 further comprises an interior surface 16 which defines the outer boundary of internal lumen 19. In some embodiments, interior surface 16 is configured to reduce stagnant flow of an infusate through interior lumen 19. In general, interior lumen 19 is in fluid communication with a fluid pathway 32 of intravenous tubing 30 and intravenous catheter 20, such that an infusate is permitted to freely flow from intravenous tubing 30 to intravenous catheter 20 via fluid chamber 10.

In some embodiments, fluid chamber 10 further comprises an access window 60 which is formed through a sidewall 62 of fluid chamber 10. In some embodiments, access window 60 comprises a cylinder which extends inwardly into interior lumen 19. Access window 60 is generally sized and shaped to house a portion of UV-C source 50, whereby UV-C radiation emitted by UV-C source 50 is permitted to pass through access window 60 to interact with an infusate present within interior lumen 19. In some embodiments, access window 60 comprises a UV-C transparent material to permit irradiation of pathogens present within interior lumen 19 and an infusate. For example, in some embodiments access window 60 comprises an optical grade quartz or fluorinated polymer material.

In some embodiments, fluid chamber 10 further comprises a UV-C opaque material or coating to prevent the emitted UV-C radiation from passing through sidewalls 62. As such, the patient or physician is prevented from being irradiated during the infusion procedure. In some embodiments, intravenous catheter 20 and intravenous tubing 30 are further coated with or wrapped in a UV-C opaque material to prevent exposure to UV-C radiation which may leak through proximal end 12 and distal end 14 openings of fluid chamber 10.

In some embodiments, interior surface 16 of fluid chamber 10 further comprises a UV-C reflective material 70, such as Gore® Diffuse Reflector Product, SolarBrite Reflective Material, or other materials with high UV-C reflective properties. UV-C reflective material 70 is provided to retain and reflects the UV-C radiation emitted by source 50 within interior lumen 19. As such, the radiant UV-C energy propagates through access window 60 and is retained within interior lumen 19. In some embodiments, exterior surface 18 comprises a UV-C reflective material (not shown) such that the UV-C energy is permitted to pass through sidewall 62 of fluid chamber 10 and is reflected back into interior lumen 19.

UV-C reflective material 70 permits the use of biocidal lamps 80 which require less power, such as UV-C LED lamps. As such, some embodiments of the present invention provide a more cost effective device. Further, use of UV-C reflective material 70 provides greater intensity and exposure of UV-C radiation to the infusate thereby resulting in efficient irradiation of microbes in the infusate during real-time flow through the infusion system 40.

For example, some embodiments of the present invention provided an unexpected result of a 99.99% kill rate of *Staphylococcus epidermidis* at 1 ml/sec flow rate with 60,000 mW-sec/cm$^2$ UV-C radiation. Mathematical models predict an incomplete kill at those radiation levels. Thus, some embodiments of the present invention provide unexpected results which show increased kill rates which are unable to be predicted using mathematical models.

As an infusate flows through interior lumen 19, the infusate is irradiated by UV-C radiation which is emitted by UV-C source 50. In some embodiments, UV-C source 50 comprises a biocidal lamp 80 which is provided in a housing 52 having a compartment for storing a battery 54 or other power source necessary to power lamp 80. In some embodiments, UV-C source 50 further comprises a control switch (not shown) by which lamp 80 is selectively powered by battery or batteries 54. In some embodiments, housing 52 comprises a UV-C opaque material. Further, in some embodiments housing 52 comprises a flange 56 which acts as a shield to further prevent UV-C radiation leakage from access window 60.

Figure 3:
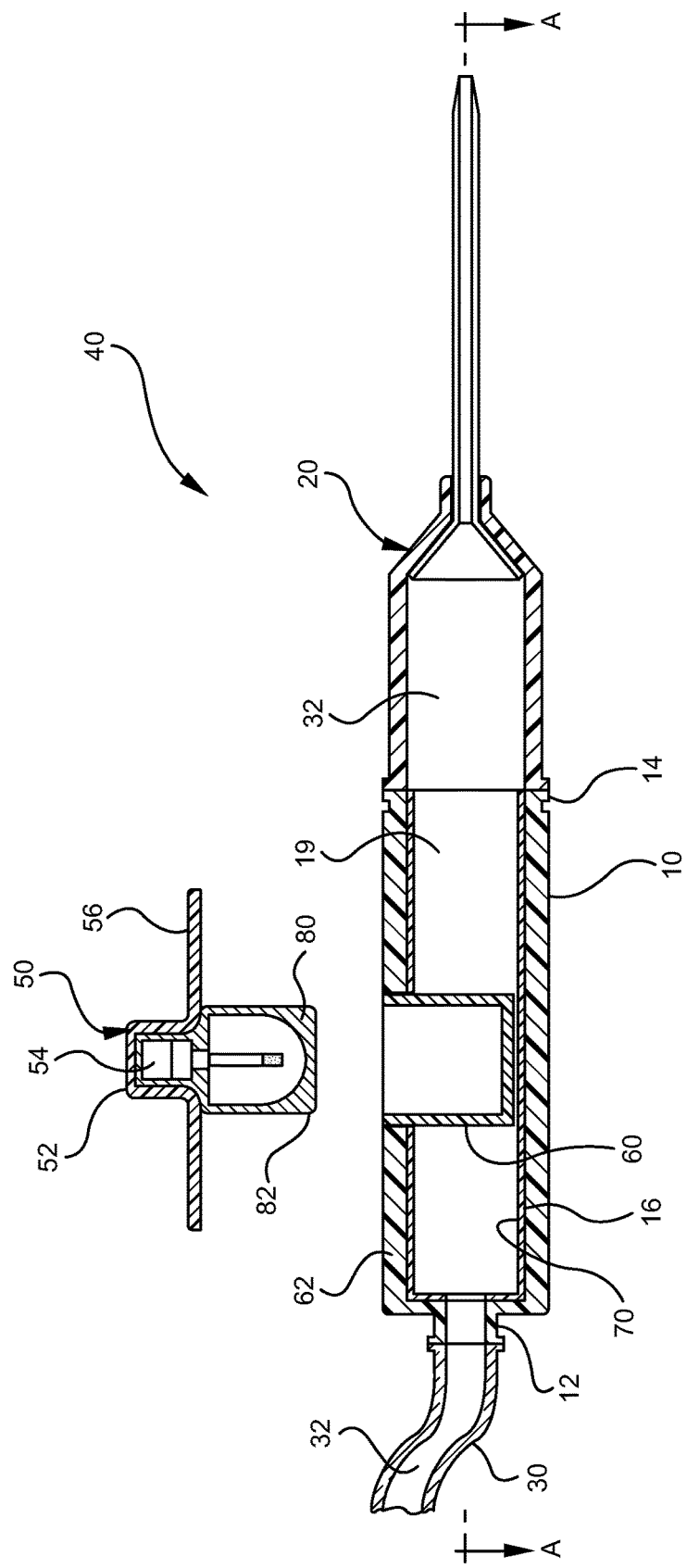
FIG. 3 is a cross section side view of a fluid chamber coupled to an intravenous catheter showing a removed UV-C radiation source in accordance with a representative embodiment of the present invention.

Referring now to FIG. 3, fluid chamber 10 is shown following removal of UV-C source 50 from access window 60. In some embodiments lamp 80 is further housed in a lens 82 which is provided to protect lamp 80. As with access window 60, lens 82 is UV-C transparent so as to enable penetration of UV-C energy into internal lumen 19. In some embodiments, access window 60 is positioned within interior lumen 19 such that a gap is maintained between a bottom portion of access window 60 and interior surface 16 or UV-C reflective material 70. As such, infusate is permitted to flow under access window 60 thereby enabling further irradiation of the infusate as it flows through fluid chamber 10.

Figure 4A:
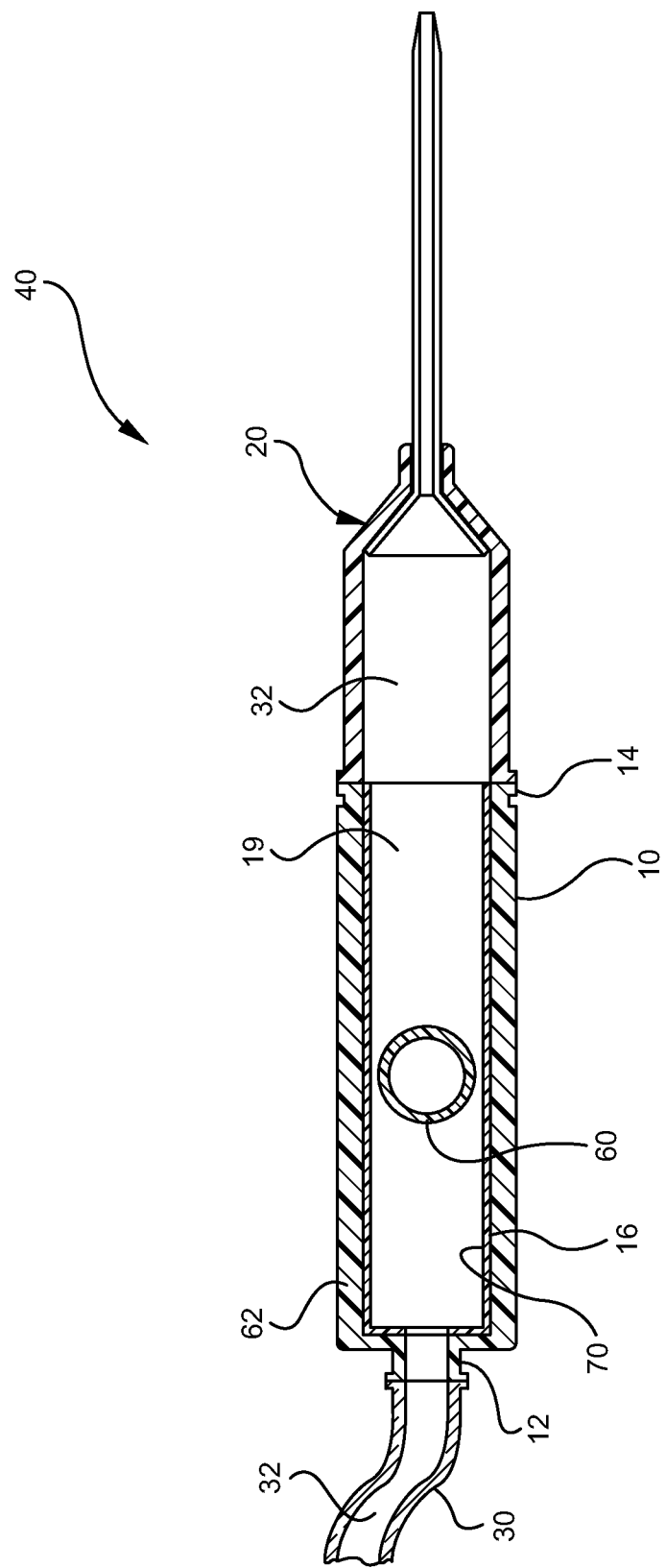
FIG. 4A is a cross section top view of the fluid chamber of FIG. 3 taken along lines A-A in accordance with a representative embodiment of the present invention.

Referring now to FIG. 4A a cross section of the infusion system 40 FIG. 3 is shown taken along lines A-A. In some embodiments, access window 60 is further positioned within interior lumen 19 such that a gap is maintained between the side portions or outer surfaces of access window 60 and interior surface 16 or UV-C reflective material 70 of fluid chamber 10. As such, infusate is permitted to flow around access window 60 thereby ensuring maximum exposure of the infusate to the UV-C radiation which is emitted through access window 60.

In some embodiments, UV-C source 50 is removable from fluid chamber 10 such that it may be reused in additional infusion systems 40 during subsequent infusion procedures. In other embodiments, UV-C source 50 is integrated into a single-use infusion system, wherein the UV-C source is disposed of with the infusion system. Further, in some embodiments the UV-C source is integrated into a fluid chamber that is reusable. For example, following catheterization of the patient the reusable fluid chamber 10 and integrated UV-C source is attached to the disposable intravenous catheter 20.

Figure 4B:
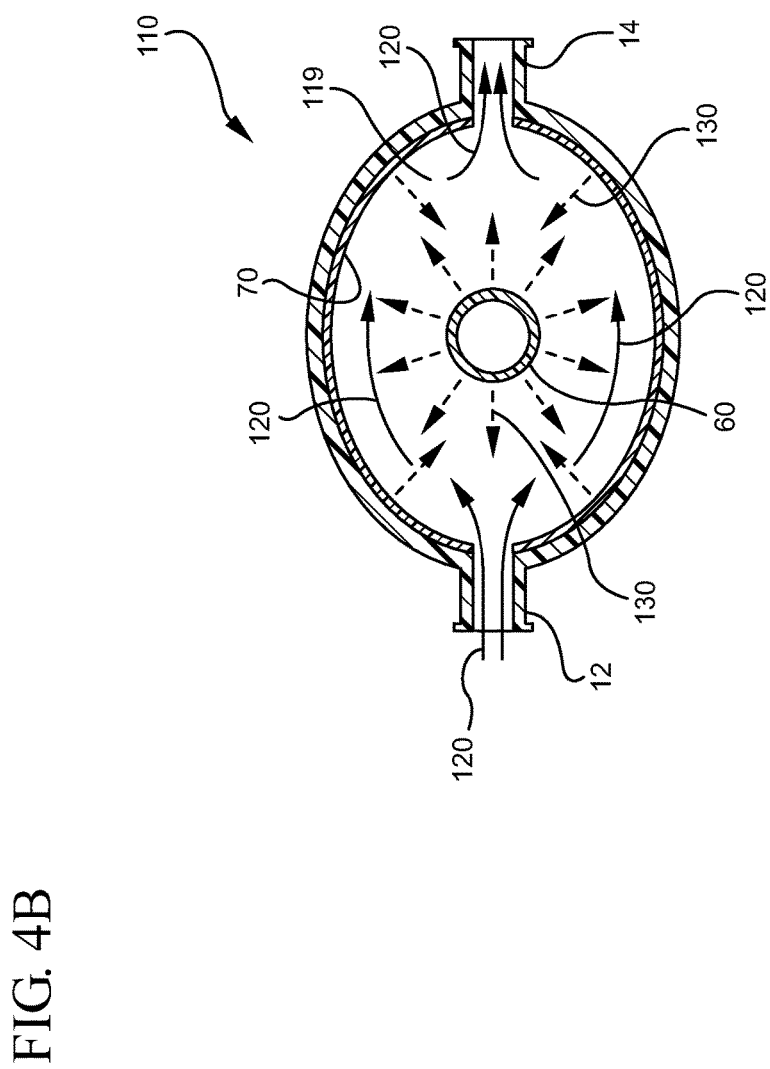
FIG. 4B is a cross section top view of a fluid chamber in accordance with a representative embodiment of the present invention.

Fluid chamber 10 may include any size, shape, material and/or configuration necessary to maximize irradiation of an infusate at real-time flow rates during an infusion procedure. Referring now to FIG. 4B, a cross section of a fluid chamber 110 is shown. In some embodiments, interior lumen 119 is configured to maximize flow rate of an infusate 120 while minimizing aberrant flow paths and maximizing irradiation of pathogens within the infusate. One such configuration is shown in FIG. 4A. As the infusate 120 enters interior lumen 119, the infusate's flow path is diverted around access window 60 thereby maximizing exposure of infusate 120 to the UV-C radiation 130. The UV-C reflective material 70 further increases the exposure of infusate 120 to UV-C radiation 130 as the radiation 130 is reflected away from interior surface 116 and back into the flow path of infusate 120.

Figure 4C:
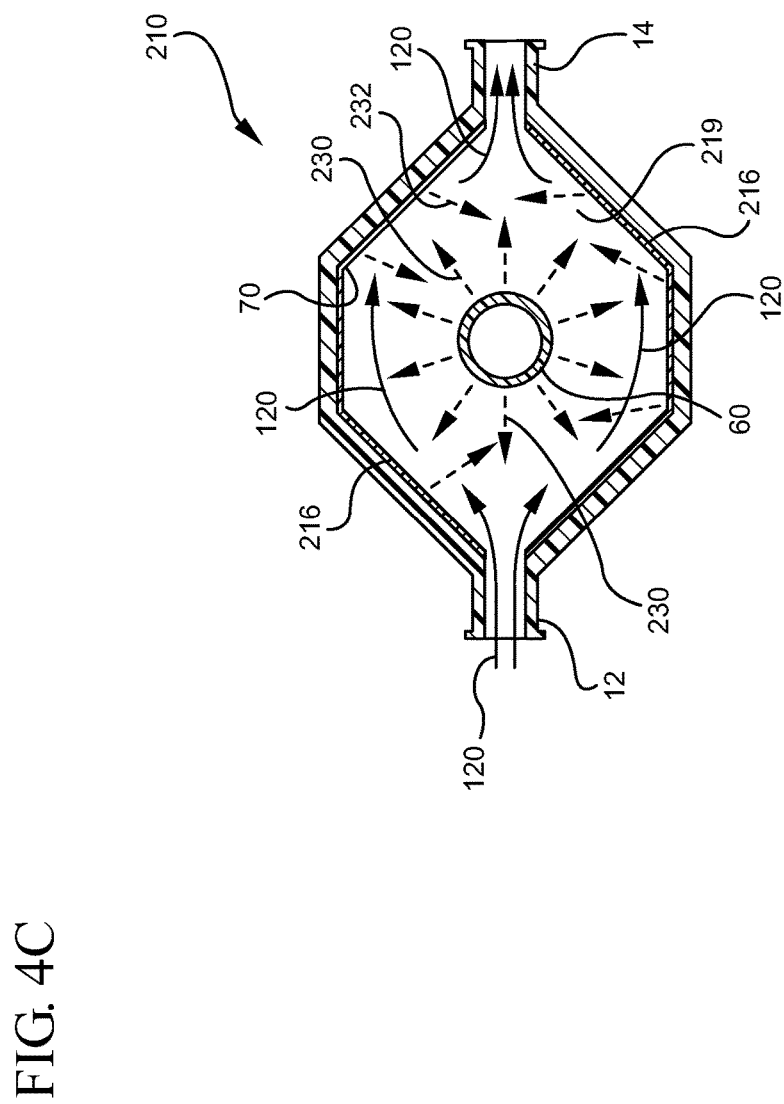
FIG. 4C is a cross section top view of a fluid chamber in accordance with a representative embodiment of the present invention.

Another configuration of a fluid chamber 210 is shown in FIG. 4C. In some embodiments, interior surface 216 is angled such that UV-C energy or radiation is emitted at a first angle 230 and reflected off of UV-C reflective material 70 at a second angle 232. Thus, in some embodiments the size, shape and configuration of fluid chamber 210 is configured to maximize the scattering of emitted and reflected UV-C radiation within interior lumen 219. These configurations further enhance the exposure of infusate 120 to UV-C radiation 230 and 232.

Figure 5:
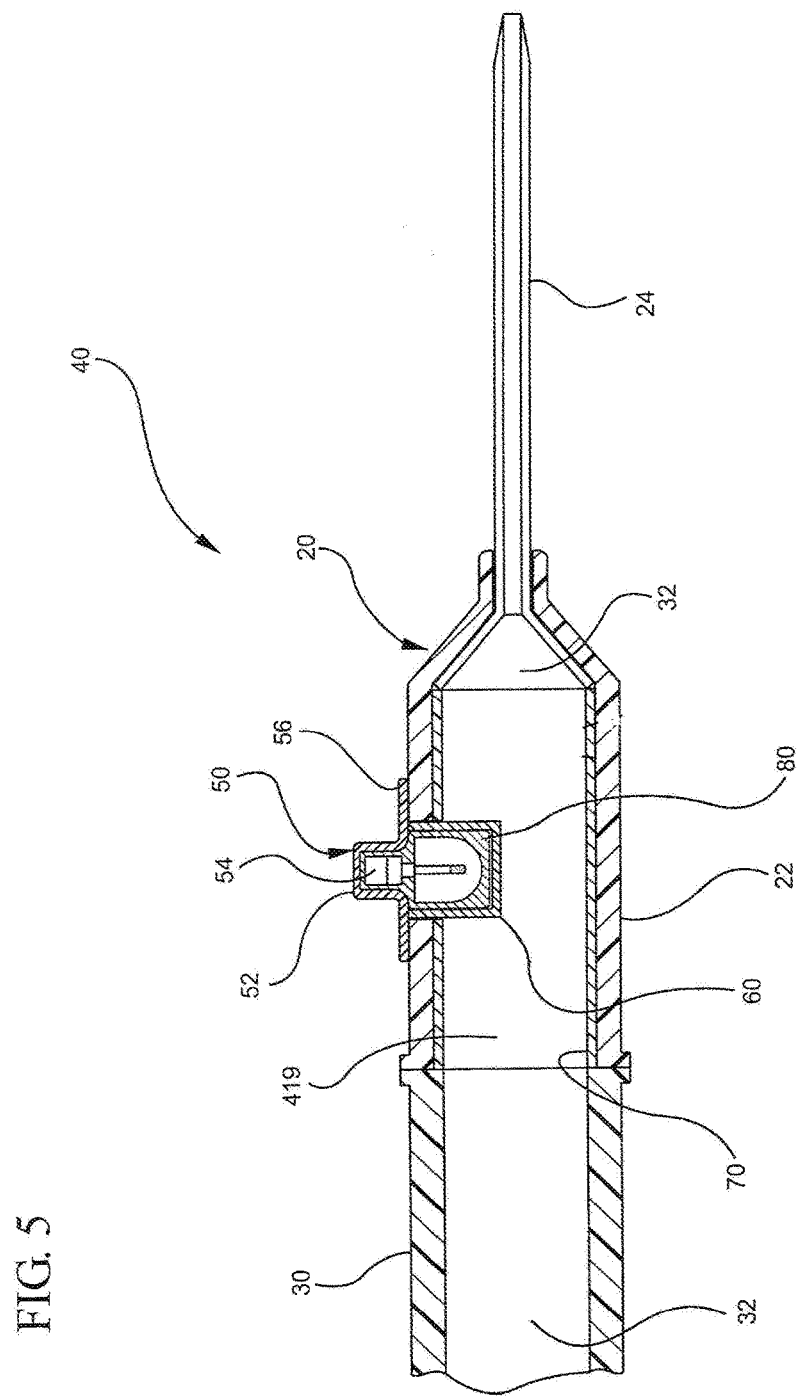
FIG. 5 is a cross section side view of an intravenous catheter and UV-C radiation source in accordance with a representative embodiment of the present invention.

Referring now to FIG. 5, a cross section of a catheter adapter 22 having an access window 60 is shown. In some embodiments, a catheter adapter 22 of an intravenous catheter 20 is configured to include an access window 60 whereby to receive a source of UV-C radiation 50. Thus, an infusion system 400 is provided which does not include a dedicated fluid chamber device. As with some of the previous embodiments, access window 60 is positioned such that a portion of access window 60 extends inwardly into an interior lumen 419 of catheter adapter 22 and terminates at an access window endwall at a first radial position within the interior lumen 419. In this embodiment, the depth to which access window 60 extends into interior lumen 419 is limited by the access window endwall within the interior lumen 419 to enable passage of an introducer needle (not shown) through interior lumen 419 and catheter tube 24. Catheter adapter 22 further comprises a UV-C reflective material 70 which lines or covers an interior surface 416 of the adapter 22. Catheter adapter 22, catheter tube 24 and intravenous tubing 30 may further comprise a UV-C opaque material or covering to prevent exposure to UV-C radiation, as discussed previously.

Figure 6:
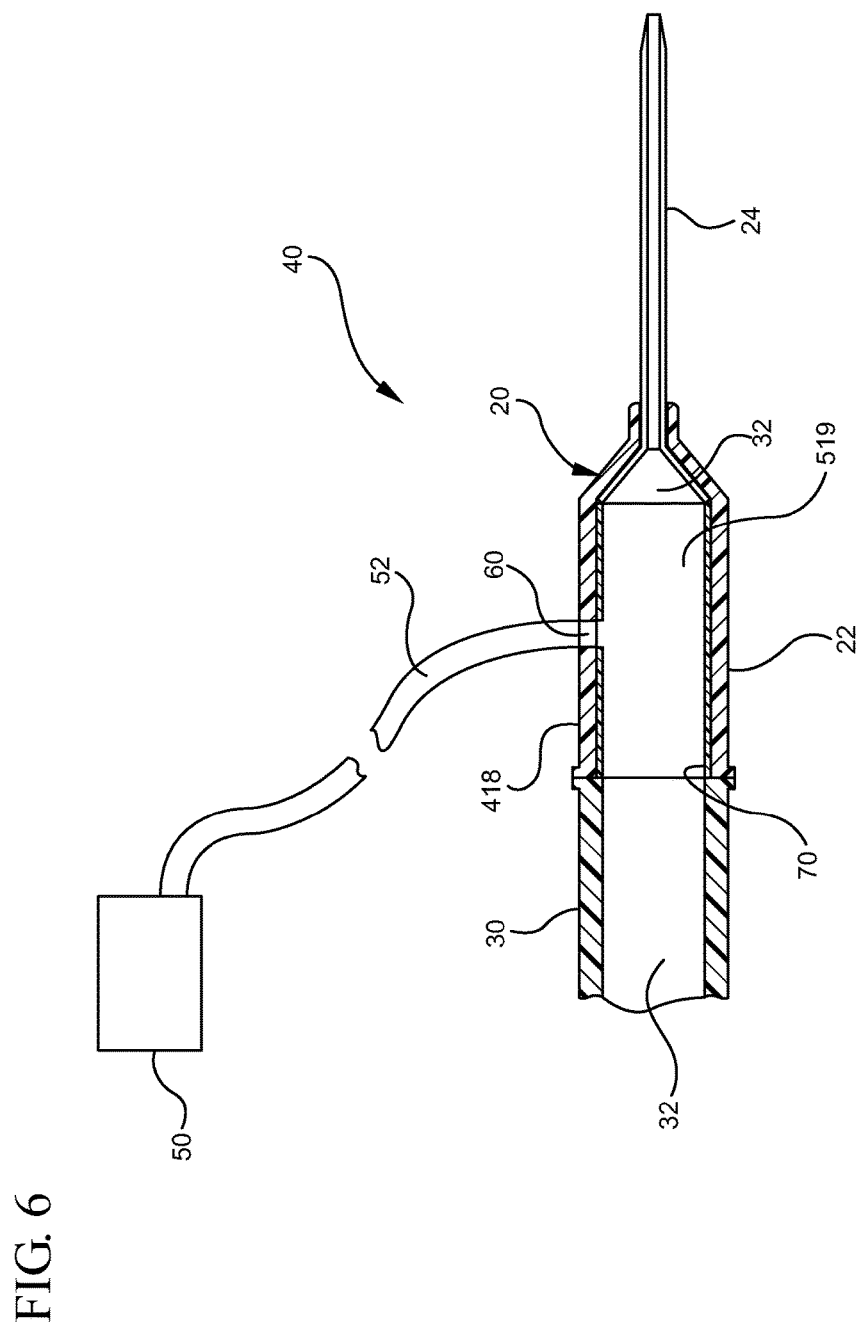
FIG. 6 is a cross section side view of a fluid chamber coupled to an intravenous catheter and a remotely located UV-C radiation source in accordance with a representative embodiment of the present invention.

In some embodiments, access window 60 does not extend into interior lumen 19, but rather forms a portion of sidewall 62, as shown in FIG. 6. The source of UV-C 50 is therefore aligned with the access window such that the UV-C radiation is emitted though the access window and into the interior lumen 519 of the catheter adapter 22. Further, in some embodiments the source of UV-C radiation 50 is a remote unit, wherein the UV-C radiation is delivered to infusion system 500 via a fiber optic cable 52 which is coupled to access window 60. Alternatively, a UV-C radiation source is provided which comprises a sleeve housing (not shown) which is slidably positioned over the exterior surface 418 of catheter adapter 22, such that the biocidal lamp is aligned with access window 60.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vascular access device, comprising:
   a catheter adapter having a proximal end comprising a proximal opening, a distal end comprising a distal opening, and an interior lumen forming a fluid chamber interposed therebetween, the interior lumen being defined by a sidewall that extends between the proximal and distal ends, the proximal opening and the distal opening providing access to the interior lumen, the catheter adapter further comprising an access window that extends inwardly from the sidewall into the interior lumen and terminates at an access window endwall at a first radial position within the interior lumen, the access window comprising UV-C transparent material such that UV-C radiation incident upon the access window is transmitted through the access window and into the interior lumen;
   a catheter having a distal end configured to be inserted into a patient's vasculature and a proximal end that extends into the distal end of the catheter adapter; and
   a source of UV-C radiation positioned in proximity to the access window such that UV-C radiation is emitted from the source of UV-C radiation and into the interior lumen of the fluid chamber via the access window to repress pathogenic activity in the catheter adapter;
   wherein the first radial position to which the access window extends is radially spaced from a longitudinal axis of the catheter adapter to thereby allow an introducer needle to extend through the catheter adapter and the catheter.

2. The vascular access device of claim 1, wherein the sidewall comprises a UV-C reflective material.

3. The vascular access device of claim 1, wherein an exterior surface of the catheter adapter comprises a UV-C opaque material.

4. The vascular access device of claim 1, wherein the access window has a cylindrical shape.

5. The vascular access device of claim 4, wherein the source of UV-C radiation comprises a lamp, and wherein the lamp extends into the access window.

6. The vascular access device of claim 1, further comprising a housing coupled to the catheter adapter around the access window, the housing containing the source of UV-C radiation.

7. The vascular access device of claim 6, wherein the housing comprises a flange which extends along an exterior surface of the catheter adapter.

8. The vascular access device of claim 6, wherein the housing contains one or more batteries for powering the source of UV-C radiation.

9. The vascular access device of claim 1, wherein the source of UV-C radiation comprises an LED lamp.

10. The vascular access device of claim 1, further comprising intravenous tubing, wherein the proximal end is coupled with the intravenous tubing, wherein a fluid pathway comprises the intravenous tubing, the fluid chamber, and the catheter, wherein fluid in the fluid pathway flows from the intravenous tubing to the catheter via the fluid chamber.

11. An intravenous catheter assembly comprising:
    a catheter adapter having a proximal end comprising a proximal opening, a distal end comprising a distal opening, and an interior lumen forming a fluid chamber interposed therebetween, the proximal opening and the distal opening providing access to the interior lumen, the interior lumen being defined by a sidewall that extends between the proximal and distal ends, the catheter adapter further comprising an access window that extends inwardly from the sidewall into the interior lumen and terminates at an access window endwall at a first radial position within the interior lumen, the access window comprising UV-C transparent material such that UV-C radiation incident upon the access window is transmitted through the access window and into the interior lumen;
    a catheter having a distal end configured to be inserted into a patient's vasculature and a proximal end that extends into the distal end of the catheter adapter, wherein the first radial position to which the access window extends is radially spaced from a longitudinal axis of the catheter adapter to thereby allow an introducer needle to extend through the catheter adapter and the catheter; and a source of UV-C radiation contained within the access window such that UV-C radiation is emitted from the source of UV-C radiation and into the interior lumen of the fluid chamber via the access window to repress pathogenic activity in the catheter adapter.

12. The intravenous catheter assembly of claim 11, wherein the sidewall comprises a UV-C reflective material.

13. The intravenous catheter assembly of claim 11, wherein an outer surface of the catheter adapter comprises a UV-C opaque material.

14. The intravenous catheter assembly of claim 11, wherein the source of UV-C radiation is an LED.

15. A method for manufacturing a vascular access device, the method comprising:

providing a catheter adapter having a proximal end comprising a proximal opening, a distal end comprising a distal opening, and an interior lumen forming a fluid chamber interposed therebetween, the proximal opening and the distal opening providing access to the interior lumen, the interior lumen being defined by a sidewall that extends between the proximal and distal ends;

providing an access window that extends inwardly from the sidewall into the interior lumen and terminates at an access window endwall at a first radial position within the interior lumen, the access window comprising UV-C transparent material such that UV-C radiation incident upon the access window is transmitted through the access window and into an interior lumen of the fluid chamber;

providing a catheter having a distal end configured to be inserted into a patient's vasculature and a proximal end that is contained within the distal end of the catheter adapter; and providing a source of UV-C radiation positioned in proximity to the access window such that UV-C radiation is emitted from the source of UV-C radiation and into the interior lumen of the fluid chamber via the access window to repress pathogenic activity in the catheter adapter;

wherein the first radial position to which the access window extends is radially spaced from a longitudinal axis of the catheter adapter to thereby allow an introducer needle to extend through the catheter adapter and the catheter.

* * * * *